United States Patent
Hu et al.

(10) Patent No.: US 11,591,303 B2
(45) Date of Patent: Feb. 28, 2023

(54) METHOD AND SYSTEM FOR PRODUCING EPOXYALKANE

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Song Hu, Shanghai (CN); Shuai Hu, Shanghai (CN); Weisheng Yang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 298 days.

(21) Appl. No.: 16/768,662

(22) PCT Filed: Nov. 30, 2018

(86) PCT No.: PCT/CN2018/118506
§ 371 (c)(1),
(2) Date: May 30, 2020

(87) PCT Pub. No.: WO2019/105451
PCT Pub. Date: Jun. 6, 2019

(65) Prior Publication Data
US 2021/0163433 A1   Jun. 3, 2021

(30) Foreign Application Priority Data

Nov. 30, 2017 (CN) .......................... 201711237459.3
Nov. 30, 2017 (CN) .......................... 201711239603.7
(Continued)

(51) Int. Cl.
C07D 301/32 (2006.01)
B01D 3/40 (2006.01)
(Continued)

(52) U.S. Cl.
CPC ........... *C07D 301/32* (2013.01); *B01D 3/322* (2013.01); *B01D 3/40* (2013.01); *B01D 17/0214* (2013.01)

(58) Field of Classification Search
None
See application file for complete search history.

(56) References Cited

U.S. PATENT DOCUMENTS 3,337,620 A * 8/1967 Null ..................... C07C 51/252
203/88
3,350,416 A * 10/1967 Null ..................... C07D 301/32
203/16
(Continued)

FOREIGN PATENT DOCUMENTS

CN   1633424 A   6/2005
CN   1678600 A   10/2005
(Continued)

*Primary Examiner* — Tam M Nguyen
(74) *Attorney, Agent, or Firm* — Novick, Kim & Lee, PLLC; Allen Xue (57) ABSTRACT

A method for producing epoxyalkane includes the step of separating, in a separation column, a stream containing epoxyalkane, extractant, and diol. The separation column operates under conditions so as to enable the extractant and the diol to form an azeotrope, and a stream containing extractant and binary azeotrope is extracted from the side-draw of the separation column to liquid-liquid separation. The method can be used for the industrial production of epoxyalkane.

23 Claims, 3 Drawing Sheets

(30) Foreign Application Priority Data

Nov. 30, 2017 (CN) .......................... 201711241136.1
Nov. 30, 2017 (CN) .......................... 201711241161.X (51) Int. Cl.
*B01D 3/32* (2006.01)
*B01D 17/02* (2006.01)

(56) References Cited

U.S. PATENT DOCUMENTS

| | | |
|---|---|---|
| 4,304,639 A | 12/1981 | Hardy et al. |
| 4,402,794 A | 9/1983 | Nemet-Mavrodin et al. |
| 4,772,732 A | 9/1988 | Huang et al. |
| 5,529,667 A | 6/1996 | Coffey |
| 6,407,279 B1 * | 6/2002 | Buchanan ............ C07C 29/1285 558/260 |
| 2006/0161010 A1 * | 7/2006 | Gobbel ................ C07D 301/12 549/531 |
| 2008/0289948 A1 * | 11/2008 | Diefenbacher ........ B01D 3/148 203/18 |

FOREIGN PATENT DOCUMENTS

| | | |
|---|---|---|
| CN | 101006067 A | 7/2007 |
| CN | 102093316 A | 6/2011 |
| CN | 104109137 A | 10/2014 |
| CN | 105294604 A | 2/2016 |
| JP | S5646874 B2 | 4/1981 |
| JP | S59024982 B2 | 2/1984 |

* cited by examiner

METHOD AND SYSTEM FOR PRODUCING EPOXYALKANE

FIELD OF THE INVENTION

The invention relates to a method for producing epoxyalkane and an epoxyalkane production system used for the method.

BACKGROUND OF THE INVENTION 1,2-butylene oxide (BO) is a homologue with ethylene oxide (EO) and propylene oxide (PO), and its molecular formula is $C_4H_8O$ (CAS number:106-88-7). It is a substance having a three-membered ring structure and active chemical properties, and is mainly used as intermediates for polyether polyol monomers and other synthetic materials. 1,2-butylene oxide can also be used for producing foam plastics, synthetic rubbers, non-ionic surfactants and so on. It can replace acetone as a diluent for nitro paint, and may be further applied as a standard substance for chromatographic analysis.

As an epoxyalkane, the BO has a larger number of —$CH_2$— functional groups in the molecular structure than EO and PO. When the BO is applied as a monomer for synthesizing a polyether polyol, its product exhibits excellent hydrophobic properties and may be especially suitable for water-repellent coating on the outer surface of some buildings and equipment with stringent requirements. In addition, the polyurethane materials synthesized by copolymerizing BO applied as monomers have excellent cold resistance, and are especially suitable for severe cold areas.

The epoxyalkane products have strict requirements on the concentrations of water, aldehydes and isomers. Water will affect the hydroxyl value and foaming properties of polymers. Aldehydes will cause the product to emit odors and affect people's health. The isomers are end-capping reagent for polymerized long-chains. Therefore, the national standards and enterprise standards in China impose strict requirements on the product purity.

According to the BASF enterprise standards, the quality and purity requirements of the qualified product of 1,2-butylene oxide are as follows: the content of BO ≥99.5%, the content of BO isomers ≤0.2%, the content of total aldehydes ≤0.05%, and the content of water ≤0.03%.

The quality and purity requirements of the superior product of 1,2-butylene oxide are as follows: the content of BO ≥99.9%, the content of BO isomers ≤0.1%, the content of total aldehydes ≤0.015%, and the content of water ≤0.005%.

The crude epoxyalkane produced by the reaction usually contains impurities such as water, methanol, acetone and methyl formate; because these impurities form an azeotrope with the epoxyalkane or the relative volatility is close to 1, it is difficult to reach the epoxyalkane product standards for BO purity through the ordinary distillation process. The purification of epoxyalkanes generally uses C7-C20 straight and branched chain hydrocarbons and/or diols as the extractant. For economic reasons, the purification process of epoxyalkanes uses a mixture of C8 straight and branched chain alkanes as the extractant. An addition of the extractant makes the relative volatility of acetaldehyde, water, methanol and methyl formate in regard to epoxyalkane to become larger, the acetaldehyde, water, methanol, and methyl formate are removed from the top of the column, and the extractant is recycled.

The butylene epoxidation products are primarily BO and its isomers such as 1,4-butylene oxide, 2,3-butylene oxide and epoxy iso-butane. Due to the presence of water, BO and its isomers will inevitably be hydrolyzed during the refining process of butylene oxide to generate 1,2-butanediol and the corresponding diol, and the hydrolysis reaction continues over time.

If the diols in the extractant is not separated and removed, it will persistently accumulate and cause a excessively high diol content in the circulating extractant, thus the extraction efficiency of the extractant will decrease and even losing the extraction ability. However, diols are mostly soluble in water and organic solvents such as butylene oxide. The diol can be removed by water washing in the liquid-liquid phase separation process, but the removal efficiency is low, and the removal process also exacerbates hydrolysis of the butylene oxide, thereby causing loss of the BO product.

Moreover, given that the boiling point of the diol is higher than the extractant C8 hydrocarbons, the diol is accumulated and circulated simultaneously with the extractant when the extractant is recycled in the system, thereby reducing the extraction efficiency of the extractant. As a result, it is necessary to reduce concentration of diol in the extractant.

In addition, 1,2-butylene oxide is hydrolyzed to form 1,2-butanediol, and the solubility of 1,2-butanediol in water is less than BO.

1,2-butene oxide reacts with methanol to form 1-butanediol monomethyl ether (ether bond is formed on the carbon atom of the terminal epoxy group), 2-butanediol monomethyl ether (ether bond is formed on the carbon atom of the 2-position epoxy group). In addition, both 1-butanediol monomethyl ether and 2-butanediol monomethyl ether are slightly soluble in water.

1,2-butene oxide may subject to polymerization reaction to form polymers, such as dimeric butylene oxide and polybutylene oxide.

1,2-butene oxide is reacted with active hydrogen-containing compounds such as water, dihydric alcohol or polyhydric alcohol to form poly-1,2-butanediol ether and derivatives thereof. The poly-1,2-butanediol ether and derivatives thereof are non-volatile viscous liquids, colorless to brown, and mostly soluble in ketones, alcohols, esters, hydrocarbons and halogenated hydrocarbons; the poly-1,2-butanediol ether and derivatives thereof having lower molecular weight are soluble in water, the water solubility decreases along with an increased molecular weight and the raised temperature.

Most of the above-mentioned reaction by-products and derivatives are hardly soluble in water and cannot be removed by water washing. When an extractive distillation method is used for refining the BO, the by-products and derivatives will accumulate in the extractant, thereby reducing the extraction efficiency of the extractant. Therefore, it is necessary to reduce the concentration of the by-products and derivatives in the extractant.

For example, U.S. Pat. No. 4,402,794 discloses the use of hydrocarbons having 7-9 carbon atoms, preferably N-octane as the extractant for a single extractive rectification to separate water, methanol, acetone, methyl formate and other impurities contained in the crude BO solution. The organic layer layered by the phase separator at the top of the extractive distillation column is delivered to the rectification column for distillation and separation of methanol and acetone, etc.; the column kettle stream from the extractive distillation column is sent to the extractive rectification column; a part of the column kettle liquid from the extractive rectification column is discharged. In this method, the column kettle liquid containing the extractant and 1,2-butanediol is discharged to alleviate its accumulation in the extractant. Due to the low content of 1,2-butanediol in the discharge stream of the column kettle, a large amount of extractant must be discharged in order to ensure purity of the extractant, thus a large amount of extractant will be lost.

U.S. Pat. No. 4,772,732 discloses a method for purifying butylene oxide by using an anion exchange resin and an adsorbent. The anion exchange resin removes acid and dehydrogen impurities while the adsorbent removes water from the impurities of butylene oxide. Depending upon the impurity level, the purification steps can be conducted singularly or in combination, and the process can proceed either batchwise in a reactor or continuously in a column. The ion exchange resin of the choice is a sulfonated macroreticular anion exchange resin and the adsorbent of choice is a molecular sieve. The method is costly, the adsorption and desorption process is also complicated, and the processing capacity is not large.

In summary, the current status of the prior art is that there still requires a method for producing epoxyalkane with low loss and high purity of extractant, high yield of epoxyalkane and low energy consumption.

SUMMARY OF THE INVENTION

A purpose of the present disclosure is to overcome the aforementioned defects of the prior art, and provide a method for producing epoxyalkane with small loss of extractant, high purity of circulating extractant, high yield of epoxyalkane, and low energy consumption.

Specifically, a first aspect of the present disclosure relates to a method for producing epoxyalkane, the method comprises: separating, in a separation column, a first stream containing epoxyalkane, extractant and diol; producing an epoxyalkane product stream from the upper part of the separation column; and discharging the extractant mainly in a form of the column kettle stream from the lower part of the separation column, it is characterized in that the method further comprises producing a second stream containing an azeotrope of the extractant and diol from the side-draw of the separation column located lower than a feed position.

A second aspect of the present disclosure provides another method for producing epoxyalkane, the method comprises:

1) introducing the crude product stream containing epoxyalkane and the extractant stream into the first rectification column and obtaining a first stream containing epoxyalkane, extractant and diol from the column kettle of the first rectification column;

2) using the method described in the first aspect to introduce the first stream into a separation column for separation.

A third aspect of the present disclosure provides an epoxyalkane production system, the system comprises:

1) a separation column, a side-draw production outlet is provided in the middle and lower part of the column;

2) a column bottom reboiler which is arranged at the lower part of the separation column to reboil part of the bottom stream of the separation column and return it to the separation column;

3) a cooler which is in connection with the side-draw production outlet of the separation column for cooling and phase separation of the liquid phase stream extracted from the side-draw production outlet.

The inventors of the present disclosure have unexpectedly discovered that the extractant and the diol heavy component impurities can form an azeotrope, in particular, an azeotrope with low boiling point (under normal pressure, the boiling point of N-octane is 125-127° C., the boiling point of 1,2-propylene glycol is 188.2° C., and the formed azeotrope has a boiling point of 122.7° C.). The type of azeotrope is heterogeneous azeotrope. After phase separation of the azeotrope, the concentration of extractant in light phase at the upper layer reaches 99.6 wt. %, the concentration of extractant in heavy phase at the lower layer is only 12 wt. %. By extracting a part of the liquid phase stream at a specific position on the side-draw of the separation column, an azeotrope of the extractant and the diol heavy component impurities can be obtained. The azeotrope may subject to a simple cooling and phase separation to discharge the diol heavy component impurities from the extractant circulation system, such a process purifies the circulation extractant, improves purity of the extractant, reduces loss of the extractant, and increases yield of the epoxyalkane.

In addition, the foregoing epoxyalkane production method provided by the present disclosure can also reduce energy consumption.

BRIEF DESCRIPTION OF THE DRAWINGS

In the drawings, the same components are represented with the same reference signs. The drawings are not illustrated according to the actual scale.

DESCRIPTION OF THE REFERENCE SIGNS

1. First stream
2. Extractant stream
3. Epoxyalkane product stream
4. First reboiler feed stream
5. First reboiler discharge stream
6. Extractant purifier feed stream
7. Heavy component impurity stream-effluent stream
8. Extractant purifier discharge stream
9. Second stream
10. Cooled second stream
11. Light phase
12. Heavy phase
31. 1,2-Butylene oxide product stream
A. First reboiler
B. Extractant purifier
C. Separation column
D. Cooler
E. Phase separator

DETAILED DESCRIPTION OF THE PREFERRED EMBODIMENTS

The entirety of publications, patent applications, patents and other reference literatures mentioned in the description is hereby incorporated by reference herein. Unless otherwise defined, each of the technologies and scientific terminologies used in the description has meanings as commonly understood by those skilled in the art. Provided that there is a conflict, the definitions in the description shall prevail.

When the description uses the prefix "well-known among those skilled in the art", "prior art" or similar terms to define materials, substances, methods, steps, devices or components, the objects defined by the prefix cover those routinely used in the technical field when the invention is presented, but also cover those which are not commonly used at present and will become those generally recognized in the art for being suitable for the similar purposes.

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to yield one or more new numerical ranges, which should be considered as specifically disclosed herein.

Apart from the content which is explicitly stated in the context of the description, any matter or item not mentioned herein is directly applied to those well-known in the art without a need of making any change. Moreover, any embodiment described herein can be freely combined with one or more other embodiments described herein, any of the thereby formed technical solutions or technical ideas shall be regarded as a part of the original disclosure or original record of the present invention, instead of being considered as the new content which has not been disclosed or anticipated herein, unless those skilled in the art believes that the combination is obviously unreasonable.

Unless explicitly stated, the pressure mentioned in the description refers to an absolute pressure.

Unless explicitly stated in the present disclosure, the expressions "first" and "second" do not represent the order of priority, they are only used for the distinguishing purpose, for example, the expressions "first" and "second" in the terms "first stream" and "second stream" are only used for distinguishing that the two streams are not the same streams. It should be noted that the diol in the system of the present disclosure refers to a variety of substances containing two alcoholic hydroxyl groups (—OH), it is mainly generated by the reaction and separation units from the epoxyalkane and its isomers during the production process of epoxyalkane, the examples of diol may be 1,2-propanediol, 1,2-butanediol, 1,3-butanediol, 1,4-butanediol and the like. Regarding the concentration of diol in the first stream, since the epoxyalkane and its isomers are continuously hydrolyzed to generate the corresponding diol in the presence of water during the refining process, thus the concentration of diol will continuously increase along with the continuous performing of the hydrolysis reaction.

The inventors of the present disclosure have utilized the process simulation software Aspen Plus and the Non-Random Two-Liquid (NRTL) thermodynamic method to carry out a full-process simulation calculation of the above-mentioned production process of epoxyalkane. As a result, it is discovered that when the solvent ratio is within a range of 3-4, the 1,2-propanediol content in the extractant is at 0, 13 wt. % and 36 wt. % respectively, the relative volatility of PO to various impurities in the mixture decreases, that is, during a process that the 1,2-propanediol content in the circulating extractant increases, the purification of PO will become difficult until it cannot be separated. Because the generated 1,2-propanediol has a higher boiling point than the heaviest component (extractant) in the system, if a heavy separation process is used, the additional separation equipment and energy consumption are required.

The inventors of the present disclosure have also discovered that the concentration of diol gradually increases from the column top of the separation column to the column kettle, but it reaches a constant peak concentration at a certain position, and then decreases, the peak concentration is the concentration of an azeotrope formed by the diol and the extractant. Further research on the 1,2-propanediol+N-octane system discovers that the content ratio of the 1,2-propanediol and N-octane in an azeotrope are 5.65 wt. %: 94.35 wt. % under atmospheric pressure. Along with an increase of the pressure, the ratio of 1,2-propanediol component in the azeotrope increases and the azeotrope evolves into a non-uniform phase azeotrope. After a phase separation of the azeotrope, the content ratio of the 1,2-propanediol and N-octane in the light phase component is 0.38 wt. %: 99.62 wt. %; the content ratio of the 1,2-propanediol and N-octane in the heavy phase component is 88.24 wt. %:11.76 wt. %. Based on this, by extracting the azeotrope at the side-draw of the said position, the diol impurities in the circulating extractant can be effectively removed. Moreover, at a temperature of 20° C., the densities of the diol impurities and the extractant are significantly different. For example, the density of 1,2-propanediol at 20° C. is 1,036.2 kg/m$^3$, and the density of N-octane is 703.0 kg/m$^3$, the larger density difference makes it to be sufficiently possible by cooling it with a conventional cooler and performing the liquid-liquid separation by using the ordinary separation tank, there is not the need for the high-efficiency liquid-liquid separation equipment. Therefore, it is possible to extract the azeotropic stream through the side-draw of the separation column to efficiently remove the diol impurities and ensure the high purity and extraction efficiency of the circulating extractant. Moreover, by means of the simple cooling, the extractant and the diol may be separated by phase separation, so that the extractant in the azeotropic mixture from a side-draw can be easily recycled to reduce the concentration of the diol and then improve cycle life of the extractant. The position is the best and most economical extraction position for the azeotrope.

Preferably, the operating conditions of the separation column comprise: a temperature of 20-95° C., preferably 30-85° C.; a pressure of 0.02-0.4 MPaA, preferably 0.10-0.32 MPaA; and the number of theoretical plates of the separation column is 15-80, preferably 20-65, and more preferably 20-50. The number of plates is counted from the column top to the column kettle, that is, the condenser at the column top is the first theoretical plate, and the column kettle-type reboiler is the last theoretical plate.

Preferably, based on the composition and distribution of the extractant in the rectification column, the position for extracting the second stream from the side-draw of the separation column is located at the $1^{st}$-$8^{th}$ plates from the bottom, preferably the $2^{nd}$-$6^{th}$ plates from the bottom, and further preferably $2^{nd}$-$4^{th}$ plates from the bottom.

According to a preferred embodiment of the present disclosure, the epoxyalkane is propylene oxide, the diol is 1,2-propanediol, and the position where the side-draw is arranged for extracting has a temperature of 100-175° C., preferably 110-170° C.

According to another preferred embodiment of the present disclosure, the epoxyalkane is butylene oxide, the diol is 1,2-butanediol, and the position where the side-draw is arranged for extracting has a temperature of 120-150° C., preferably 125-145° C.

Particularly, when the pressure of the separation column in the present disclosure is controlled to be 0.02-0.40 MPaA, and more preferably 0.10-0.32 MPaA, the temperature of the azeotrope may be 80-180° C., and more preferably 110-170° C., it is conducive to circulation of the extractant with high purity and high yield. The inventors discovers that in the system of the present disclosure, when the operating pressure is too low, for example, less than 0.02 MPaA, the temperature at the column top of the separation column is low, and the inexpensive cooling water obtained through natural air cooling cannot be used as a cooling medium to cool the column top stream; while the operating pressure is too high, for example, when it is higher than 0.40 MPaA, the column kettle temperature of the separation column is excessively high, the propylene glycol in the system of the present disclosure will subject to dehydration, polymerization and other reactions to generate new impurities, thereby increasing the difficulty of separation.

In order to further improve the purity of the extractant, increase the yield of the epoxyalkane, and reduce the loss of the extractant, according to another specific embodiment of the present disclosure, the second stream extracted from the side-draw of the separation column is cooled and subjected to the liquid-liquid phase separation. The light phase is returned to the separation column, and the heavy phase is regarded as heavy component impurities for external extraction. The technical may significantly increase the purity of the extractant, reduce the loss of the extractant, and increase the yield of the epoxyalkane.

In order to further increase the purity of the extractant, reduce the loss of the extractant, and increase the yield of the epoxyalkane, according to a preferred embodiment, the method of the present disclosure further includes: arranging an extractant purifier between the lower part of an inlet of the separation column for introducing a first stream and the column bottom of the separation column; in addition, regarding a part of the column kettle stream of the separation column as a third part of the stream and introducing it into the extractant purifier for processing, so as to respectively obtain a vapor phase or a vapor-liquid mixture as a light component and a liquid phase as a heavy component, returning the light component to the separation column, and introducing the heavy component to a post-treatment.

For the sake of further increasing purity of the extractant in the method of the present disclosure, the third part of the stream accounts for 2-20 wt. % of the total amount of the column kettle stream of the separation column.

Further, the extractant purifier is preferably a distillation column or a second reboiler.

A preferred solution of the present disclosure is to additionally arrange a reboiler at the bottom of a conventional separation column provided with a reboiler, that is, two reboilers are configured at the bottom of the separation column. As for newly-established device, such an arrangement can save investment on equipment, reduce the amount of extractant loss and improve product quality; it is also particularly suitable for the modification and upgrading of old devices, it has small modification and low investment, and may produce an obvious effect in reducing the amount of extractant loss. Therefore, in a particularly preferred case, the extractant purifier is a second reboiler, and the second reboiler is a kettle-type reboiler.

Preferably, the height of the first reboiler and the extractant purifier relative to the column bottom of the separation column is arranged such that the temperature difference between the first reboiler and the extractant purifier is ≤5° C., Preferably ≤3° C. In the present disclosure, the main function of the extractant purifier is to purify the extractant. The ideal condition resides in that there is not temperature difference among the first reboiler, the extractant purifier and the column kettle of the separation column, however, in view of various influencing factors in the actual industrial production process, the present disclosure allows the temperature difference between the first reboiler and the extractant purifier to be ≤5° C., preferably ≤3° C.

According to a particularly preferred embodiment, both the first reboiler and the extractant purifier of the present disclosure are disposed at a column kettle of the separation column. Such an arrangement may significantly improve the purity of the extractant, reduce the loss of the extractant, and increase the yield of the epoxyalkane.

Preferably, the ratio of the heat exchange area of the first reboiler to the second reboiler is within a range of (2-5):1.

Preferably, the ratio of the extractant in the first stream to the epoxyalkane is (2-25):1, more preferably (3-20):1, and even more preferably (3-13):1, based on the percentage by weight.

The first reboiler is preferably any one of the group consisting of a thermosiphon reboiler, a kettle-type reboiler and a forced circulation type reboiler.

Preferably, the epoxyalkane is propylene oxide, butylene oxide or an isomer of butylene oxide; more preferably, the epoxyalkane is butylene oxide; particularly preferably, the epoxyalkane is 1,2-butylene oxide.

Preferably, the diol comprises a hydrolysate of an epoxyalkane and/or a hydrolysate of isomers of the epoxyalkane.

The raw material used in the production method of the present disclosure is a first stream containing epoxyalkane, extractant and diol, the first stream is preferably an extraction product stream obtained by subjecting the product from the alkene epoxidation reaction to extractive rectifying process. The purified extractant obtained in the method of the disclosure may return to the extractive rectification column for recycling.

The extractants used for the purification of epoxyalkanes are well known in the art. Generally, C7-C20 straight and branched chain hydrocarbons and/or diols are used as the extractant. For economic reasons, a mixture of C8 straight and branched chain alkanes such as N-octane, isooctane and 2-methylheptane, is used as the extractant. From the viewpoint of reducing cost of the extractant, it is preferable to select the mixture.

According to a preferred embodiment of the present disclosure, after the first stream containing the epoxyalkane, the extractant and the diol is rectified in the separation column, the column kettle stream of the separation column comprises an extractant and heavy components. Taking butylene oxide as an example, these heavy components include 1,2-butanediol, 1-butanediol monomethyl ether, 2-butanediol monomethyl ether, dimeric butylene oxide, polybutylene oxide, poly-1,2-butanediol ether and its derivatives, or mixtures thereof. Taking propylene oxide as an example, these heavy components include 1,2-propylene glycol, propylene glycol monomethyl ether, dimeric propylene oxide, polypropylene oxide, polypropylene glycol ether and its derivatives, or a mixture thereof.

Generally speaking, the separation efficiency of extractive distillation is constant when the purity of the extractant is unchanged. However, the present disclosure emphasizes that during the refining process, side reactions may occur to generate diol and its derivative impurities, and the production of the impurities is unavoidable, and the impurities will accumulate and circulate in the system. The impurities are adverse to extractive distillation and reduce the extractive efficiency of the extractant. If the extractant is directly discharged to the outside, the loss of the extractant is large as the heavy component impurity content in the extractant is relatively low. In the preferred solution of the present disclosure, merely by adding a small extractant purifier, the concentration of heavy components in the effluent stream (that is, the liquid-phase heavy component obtained in the extractant purifier) can be increased by one time or more, the amount of effluent extractant loss is reduced by more than half. By adopting the present disclosure, under the condition that the external discharge amount of the extractant is the same, the content of heavy component impurities in the circulating extractant is 50% of the direct external discharge scheme after a long period of operation. If the direct external discharge scheme is adopted, the yield of the epoxyalkane must be reduced in order to improve the product quality of the epoxyalkane, otherwise the product quality cannot be guaranteed.

The present disclosure is described in detail below with reference to the drawings, it should be noted that the protection scope of the present disclosure is not limited thereto, but being determined by the appended claims.

Figure 1:
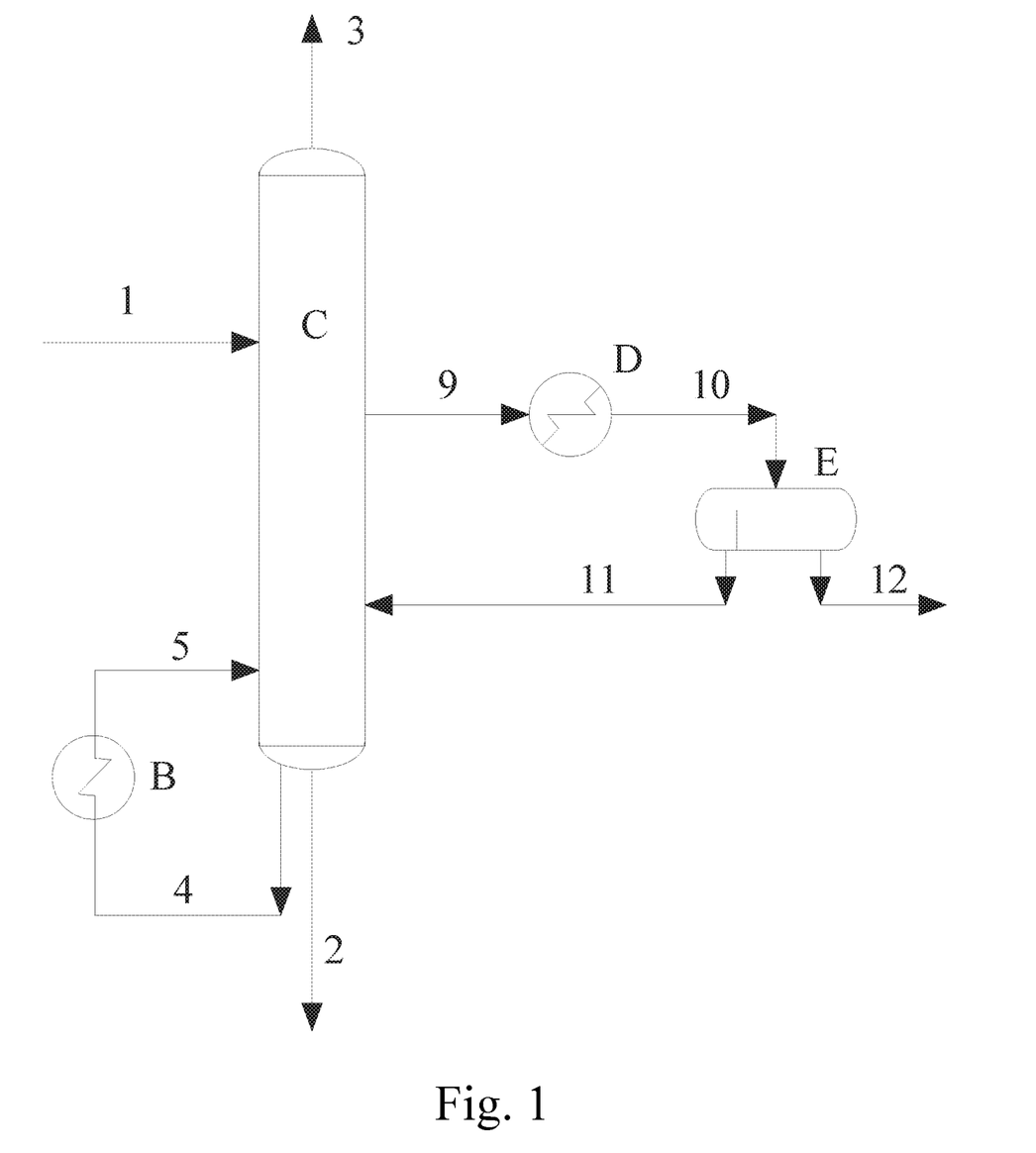
FIG. 1 is a schematic flowchart of a method according to a preferred embodiment of the present disclosure.

As illustrated in FIG. 1 of the present disclosure, a first stream 1 containing epoxyalkane, extractant and diol enters a separation column C, an epoxyalkane product stream 3 is removed from the top of the separation column, and an extractant stream 2 is removed from the bottom of the separation column, the removed extractant may return to the aforementioned extractive rectification column (not shown in the figure) for recycling. A first reboiler A is provided at the bottom of the separation column C, and the first reboiler feed stream 4 sends the column kettle liquid to the first reboiler A for heating to obtain a first reboiler discharge stream 5 and return it to a lower part of the separation column C, the second stream 9 containing the extractant and the binary azeotrope is extracted from the side-draw of the separation column C and sent to the cooler D for cooling to obtain a cooled second stream 10, and then the cooled second stream 10 enters the phase separator E (such as a conventional separation tank) to perform liquid-liquid phase separation, the light phase 11 (mainly containing the extractant) is returned to the separation column for recycling, and the heavy phase 12 (mainly containing diol) is discharged from the system.

Figure 2:
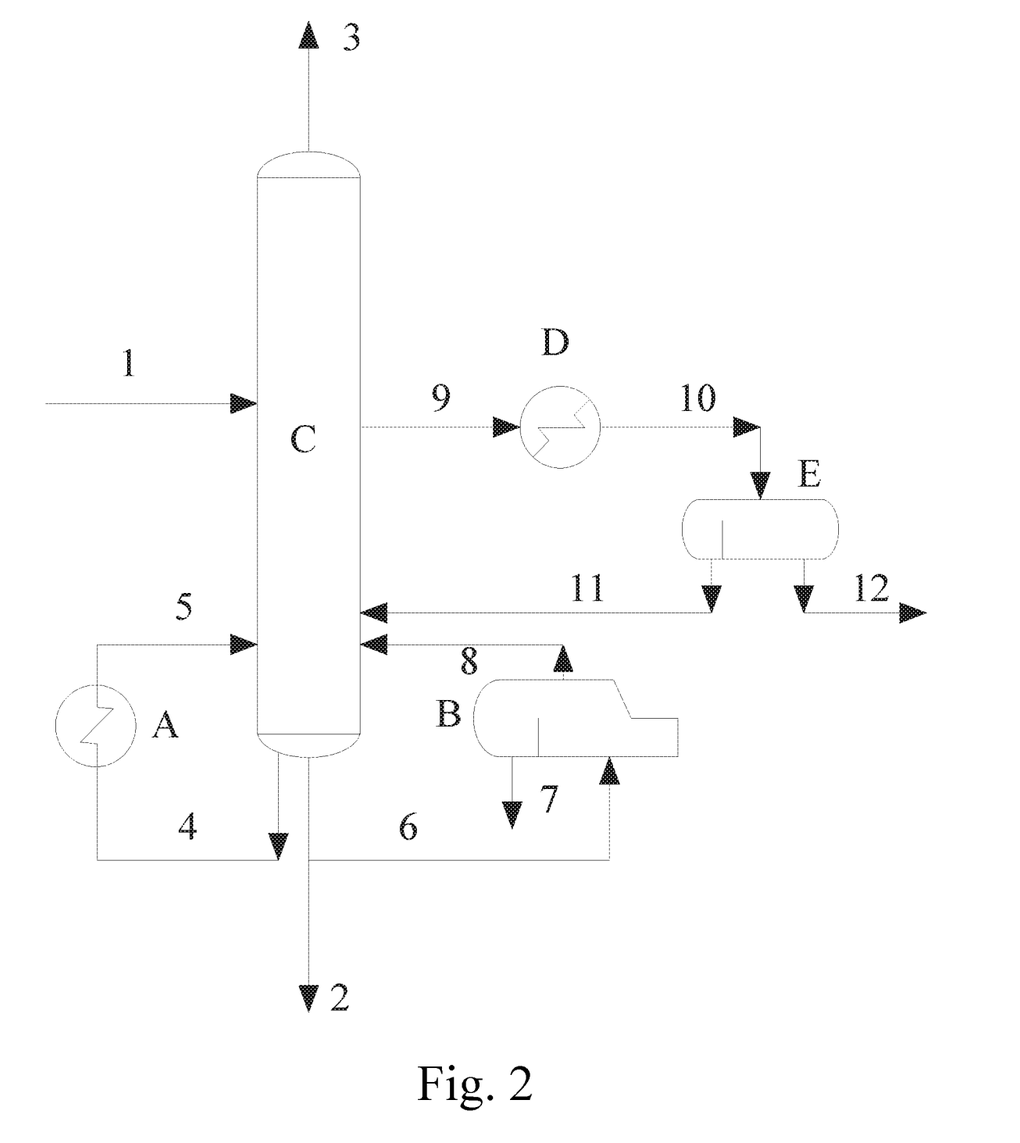
FIG. 2 is a schematic flowchart of a method according to another preferred embodiment of the present disclosure.

As illustrated in FIG. 2 of the present disclosure, a first stream 1 containing epoxyalkane, extractant and diol enters a separation column C, an epoxyalkane product stream 3 is removed from the top of the separation column, and an extractant stream 2 is removed from the bottom of the separation column, a second stream 9 containing an azeotrope of the extractant and the diol is extracted from the side-draw of the separation column C and sent to the cooler D for cooling to obtain a cooled second stream 10, and then the cooled second stream 10 enters the phase separator E to perform liquid-liquid phase separation, the light phase 11 (mainly containing the extractant) is returned to the separation column for recycling, and the heavy phase 12 (mainly containing diol) is discharged from the system; a first reboiler A and an extractant purifier B are disposed at a bottom of the separation column C, the first reboiler feed stream 4 sends a part of the column kettle liquid to the first reboiler A for heating to obtain a first reboiler discharge stream 5, the first reboiler discharge stream 5 is circulated back to a lower part of the separation column C, the extractant purifier feed stream 6 sends a part of the column kettle stream to an extractant purifier B and obtain an extractant purifier discharge stream 8 as the vapor phase light component and a heavy component impurity stream-effluent stream 7 as the liquid phase heavy component after heating, wherein the extractant purifier discharge stream 8 returns to the lower portion of the separation column C, the heavy component impurity stream-effluent stream 7 is discharged from the bottom of the extractant purifier B.

The inventors of the present disclosure have utilized the process simulation software Aspen Plus and the NRTL thermodynamic method to carry out a full-process simulation calculation of the above-mentioned production process of epoxyalkane, wherein the feed composition comprises 98.99 wt. % of propylene oxide (PO), 0.1 wt. % of acetaldehyde, 0.1 wt. % of methanol, 0.01 wt. % of methyl formate and 0.8 wt. % of water, the production scale of the plant is 100,000 tons/year of the PO product with a purity of ≥99.99 wt. %, and the annual operating time is 8,000 h; on this basis, the feed flow rate of the crude PO is 12,643 kg/h, the feed temperature is 50° C., and the feed pressure is 300 kPa. The design requirements are as follows: the flow rate of PO product is 12,500 kg/h, the PO content is ≥99.99 wt. %, the methyl formate content is ≤5 wtppm, the water content is ≤10 wtppm, and the acetaldehyde content is ≤5 wtppm.

The process conditions are shown in Table 1 below, and the experimental results are shown in Table 2.

TABLE 1

Process simulation and optimization process conditions

| Items | Parameters | Numerical values | Unit |
| --- | --- | --- | --- |
| Rectification column | Theoretical plates | 60 | — |
| | Operating pressure | 200 | kPa |
| | Feed plates for crude PO | 31 | — |
| | Solvent temperature | 50 | ° C. |
| | Solvent ratio | 4.0 | |
| | Flow rate of water | 55.0 | kg/h |
| Separation column | Theoretical plates | 30 | — |
| | Operating pressure | 170 | kPa |
| Removing propylene glycol | Temperature | 40 | ° C. |

TABLE 2

Economic analysis

| | Present disclosure | Traditional method |
| --- | --- | --- |
| Content of propylene glycol in circulating solvent | 46 wtppm | 2 wt % |
| Solvent ratio | 4.0 | 6.0 |
| Energy consumption, MW/t PO | 0.721 | 0.775 |
| Solvent loss, kg/h | 2.4 | 823.6 |
| PO yield, % | 99.88 | 99.78 |

As illustrated in the data of Table 2, when the propylene glycol content in the circulating extractant has accumulated to 2 wt %, the traditional process requires a higher solvent ratio and higher energy consumption for the sake of reaching the same product specifications. As can be seen, the process for removing diol impurities from the side-draw of the present disclosure has obvious advantages.

Figure 3:
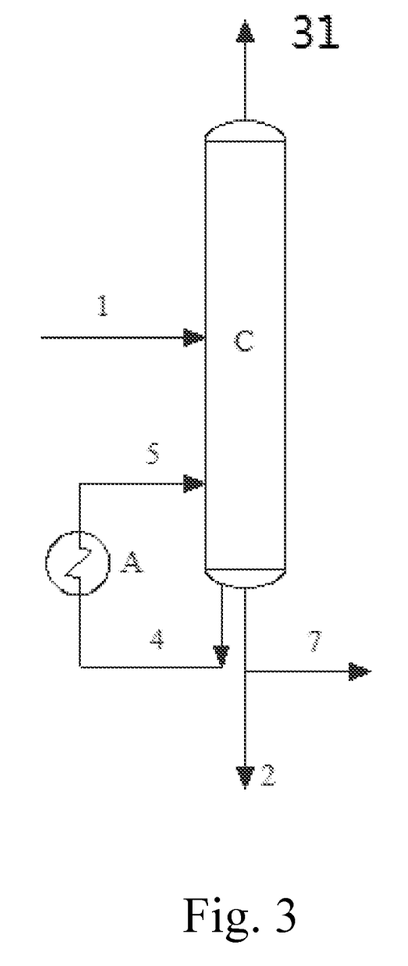
FIG. 3 is a schematic flowchart of a method provided in the prior art document U.S. Pat. No. 4,402,794.

FIG. 3 shows a prior art, a feed stream 1 containing 1,2-butylene oxide and an extractant is sent to a separation column C, the 1,2-butylene oxide product stream 31 is removed from the top of the separation column, and the extractant stream 2 is removed from the bottom of the separation column; the bottom of the separation column C is provided with a first reboiler A, the first reboiler feed stream 4 sends the column kettle liquid into the first reboiler A for heating and the first reboiler discharge stream 5 obtained after heating is sent to the lower part of the separation column C, the extractant stream 2 separates a stream as a heavy component impurity stream-effluent stream 7 to discharge from the separation system. Because the extractant and heavy components are discharged to reduce the accumulation of reaction by-products and derivatives in the extractant, a large amount of the extractant will lost.

The present disclosure further provides an epoxyalkane production system, the system comprises:

1) a separation column, a side-draw production outlet is provided in the lower part of the column;

2) a column bottom reboiler arranged at the lower part of the separation column, reboils part of the bottom stream of the separation column and returns it to the separation column;

3) a cooler in connection with the side-draw production outlet of the separation column, is used for cooling and phase separation of the liquid phase material extracted from the side-draw production outlet.

Preferably, the number of plates in the separation column is within a range of 15-80, when the number of plates is counted from the column kettle to the column top, the side-draw production outlet is located within the $1^{st}$ to $8^{th}$ plates, preferably the $2^{nd}$ to $6^{th}$ plates.

Preferably, the light phase obtained by cooling and phase separation via the cooler is returned to the separation column, and the heavy phase is discharged outside. As mentioned above, the densities of the diol impurities and the extractant are significantly different, the diol impurities and the extractant can be separated simply by cooling and phase separation. Therefore, the cooler may be a variety of devices being capable of performing the above-mentioned cooling and phase separation functions.

Preferably, the system further comprises an extractant purifier, the extractant purifier is arranged at the middle or lower part of the separation column for receiving part of the bottom material of the separation column and performing purification treatment to remove the liquid phase heavy component having a higher boiling point than the extractant, obtain the light component in vapor phase or vapor-liquid mixed phase which is mainly consisting of the extractant, and return the light component to the separation column.

The extractant purifier is preferably a reboiler, more preferably a kettle-type reboiler.

Preferably, the ratio of the heat exchange area of the column bottom reboiler of the separation column to the extractant purifier is within a range of (2-5):1. That is, the ratio of the flow rate of stream entering the column bottom reboiler to the flow rate of material entering the reboiler serving as the extractant purifier is within a range of (2-5):1.

Preferably, the number of plates in the separation column is within a range of 15-80, when the number of plates is counted from the column top to the column kettle, the feed position of the extractant purifier is located at the 0 to $4^{th}$ plates from the bottom, preferably the 0 to $2^{nd}$ plates from the bottom.

Preferably, the feed position of the extractant purifier is higher than the feed position of the bottom reboiler with 0-4 plates.

Preferably, the extractant purifier is in connection with the separation column through a pipeline.

The present disclosure will be further described below through specific examples. The results in the following examples and comparative examples are taken from the results after 800 hours of stable operation of the system. The composition of products is determined by the Chinese national standard gas chromatography GB/T9722-2006 method. The following term "wtppm" refers to the concentration of ppm by weight.

Example 1

According to the process flow shown in FIG. 1, the extractant is N-octane, and a ratio of the extractant and 1,2-butylene oxide is 12:1 in a stream containing 1,2-butylene oxide, extractant and diol based on the percentage by weight; the number of theoretical plates of the separation column is 30, the side-draw production outlet of the separation column is located at the $2^{nd}$ theoretical plate above a return port of the first reboiler. The operating pressure of the separation column is 0.10 MPaA, the temperature is 68° C., the temperature of an azeotrope extracted from the side-draw is 129° C., the diol content is 5.44 wt %, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.81%, the extractant at the bottom of the separator has a purity of 99.00%, the loss rate of the extractant is 0.043%.

Example 2

According to the process flow shown in FIG. 1, the extractant is N-octane, and a ratio of the extractant and 1,2-butylene oxide is 10:1 in a stream containing 1,2-butylene oxide, extractant and diol based on the percentage by weight; the number of theoretical plates of the separation column is 30, the side-draw production outlet of the separation column is located at the $2^{nd}$ theoretical plate above a return port of the reboiler. The operating pressure of the separation column is 0.10 MPaA, the temperature is 68° C., the temperature of an azeotrope extracted from the side-draw is 129° C., the diol content is 5.44 wt %, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.82%, the extractant at the bottom of the separator has a purity of 99.00%, the loss rate of the extractant is 0.046%.

Example 3

According to the process flow shown in FIG. 1, the extractant is N-octane, and a ratio of the extractant and 1,2-butylene oxide is 8:1 in a stream containing 1,2-butylene oxide, extractant and diol based on the percentage by weight; the number of theoretical plates of the separation column is 30, the side-draw production outlet of the separation column is located at the $2^{nd}$ theoretical plate above a return port of the reboiler. The operating pressure of the separation column is 0.10 MPaA, the temperature is 68° C., the temperature of an azeotrope extracted from the side-draw is 129° C., the diol content is 5.44 wt %, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.84%, the extractant at the bottom of the separator has a purity of 99.00%, the loss rate of the extractant is 0.047%.

Example 4

According to the process flow shown in FIG. 1, the extractant is N-octane, and a ratio of the extractant and 1,2-butylene oxide is 6:1 in a stream containing 1,2-butylene oxide, extractant and diol based on the percentage by weight; the number of theoretical plates of the separation column is 30, the side-draw production outlet of the separation column is located at the 2nd theoretical plate above a return port of the reboiler. The operating pressure of the separation column is 0.10 MPaA, the temperature is 68° C., the temperature of an azeotrope extracted from the side-draw is 129° C., the diol content is 5.44 wt %, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.83%, the extractant at the bottom of the separator has a purity of 99.00%, the loss rate of the extractant is 0.048%.

Example 5

According to the process flow shown in FIG. 1, the extractant is C8 saturated alkane mixture, and a ratio of the extractant and 1,2-butylene oxide is 6:1 in a stream containing 1,2-butylene oxide, extractant and diol based on the percentage by weight; the number of theoretical plates of the separation column is 30, the side-draw production outlet of the separation column is located at the $2^{nd}$ theoretical plate above a return port of the reboiler. The operating pressure of the separation column is 0.10 MPaA, the temperature is 68° C., the temperature of an azeotrope extracted from the side-draw is 125° C., the diol content is 5.01 wt % by weight, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.80%, the extractant at the bottom of the separator has a purity of 99.00%, the loss rate of the extractant is 0.049%.

Example 6

According to the process flow shown in FIG. 1, the extractant is N-octane, and a ratio of the extractant and 1,2-butylene oxide is 10:1 in a stream containing 1,2-butylene oxide, extractant and diol based on the percentage by weight; the number of theoretical plates of the separation column is 15, the side-draw production outlet of the separation column is located at the Pt theoretical plate above a return port of the reboiler. The operating pressure of the separation column is 0.12 MPaA, the temperature is 73° C., the temperature of an azeotrope extracted from the side-draw is 135° C., the diol content is 5.93 wt %, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.83%, the extractant at the bottom of the separator has a purity of 99.00%, the loss rate of the extractant is 0.042%.

Example 7

According to the process flow shown in FIG. 1, the extractant is N-octane, and a ratio of the extractant and 1,2-butylene oxide is 10:1 in a stream containing 1,2-butylene oxide, extractant and diol based on the percentage by weight; the number of theoretical plates of the separation column is 45, the side-draw production outlet of the separation column is located at the $3^{rd}$ theoretical plate above a return port of the reboiler. The operating pressure of the separation column is 0.13 MPaA, the temperature is 76° C., the temperature of an azeotrope extracted from the side-draw is 137.5° C., the diol content is 6.16 wt %, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.84%, the extractant at the bottom of the separator has a purity of 99.00%, the loss rate of the extractant is 0.041%.

Example 8

According to the process flow shown in FIG. 1, the extractant is N-octane, and a ratio of the extractant and 1,2-butylene oxide is 10:1 in a stream containing 1,2-butylene oxide, extractant and diol based on the percentage by weight; the number of theoretical plates of the separation column is 60, the side-draw production outlet of the separation column is located at the $4^{th}$ theoretical plate above a return port of the reboiler. The operating pressure of the separation column is 0.15 MPaA, the temperature is 77° C., the temperature of an azeotrope extracted from the side-draw is 138° C., the diol content is 6.21 wt %, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.84%, the extractant at the bottom of the separator has a purity of 99.00%, the loss rate of the extractant is 0.040%.

Example 9

According to the process flow shown in FIG. 1, the extractant is N-octane, and a ratio of the extractant and 1,2-butylene oxide is 10:1 in a stream containing 1,2-butylene oxide, extractant and diol based on the percentage by weight; the number of theoretical plates of the separation column is 65, the side-draw production outlet of the separation column is located at the $6^{th}$ theoretical plate above a return port of the reboiler. The operating pressure of the separation column is 0.17 MPaA, the temperature is 80° C., the temperature of an azeotrope extracted from the side-draw is 142° C., the diol content is 6.60 wt %, and the diol in the side-draw is enriched and extracted.

The 1,2-butylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.85%, the extractant at the bottom of the separator has a purity of 99.00%, the loss rate of the extractant is 0.039%.

Example 10

According to the process flow shown in FIG. 1, the extractant is N-octane, and a ratio of the extractant and 1,2-propylene oxide is 6:1 in a stream containing 1,2- propylene oxide, extractant and diol based on the percentage by weight; the number of theoretical plates of the separation column is 20, the side-draw production outlet of the separation column is located at the Pt theoretical plate above a return port of the reboiler. The operating pressure of the separation column is 0.10 MPaA, the temperature is 34.1° C., the temperature of an azeotrope extracted from the side-draw is 112.8° C., the diol content is 6.86 wt %, and the diol in the side-draw is enriched and extracted.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.85%, the extractant at the bottom of the separator has a purity of 99.00%, the loss rate of the extractant is 0.035%.

Example 11

According to the process flow shown in FIG. 1, the extractant is N-octane, and a ratio of the extractant and 1,2-propylene oxide is 6:1 in a stream containing 1,2-propylene oxide, extractant and diol based on the percentage by weight; the number of theoretical plates of the separation column is 30, the side-draw production outlet of the separation column is located at the $2^{nd}$ theoretical plate above a return port of the reboiler. The operating pressure of the separation column is 0.16 MPaA, the temperature is 47.9° C., the temperature of an azeotrope extracted from the side-draw is 134.8° C., the diol content is 8.14 wt %, and the diol in the side-draw is enriched and extracted.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.86%, the extractant at the bottom of the separator has a purity of 99.00%, the loss rate of the extractant is 0.030%.

Example 12

According to the process flow shown in FIG. 1, the extractant is N-octane, and a ratio of the extractant and 1,2-propylene oxide is 6:1 in a stream containing 1,2-propylene oxide, extractant and diol based on the percentage by weight; the number of theoretical plates of the separation column is 40, the side-draw production outlet of the separation column is located at the $2^{nd}$ theoretical plate above a return port of the reboiler. The operating pressure of the separation column is 0.32 MPaA, the temperature is 71.1° C., the temperature of an azeotrope extracted from the side-draw is 159.8° C., the diol content is 10.63 wt %, and the diol in the side-draw is enriched and extracted.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.87%, the extractant at the bottom of the separator has a purity of 99.00%, the loss rate of the extractant is 0.028%.

Example 13

According to the process flow shown in FIG. 2, the extractant is N-octane, and a ratio of the extractant and 1,2-propylene oxide is 12:1 in a feed stream containing 1,2-propylene oxide, extractant and heavy component impurities based on the percentage by weight; the number of theoretical plates of the separation column is 30, the side-draw production outlet of the separation column is located at the 2nd theoretical plate above a return port of the reboiler. The operating pressure of the separation column is 0.10 MPaA, the temperature is 68° C., the temperature of an azeotrope extracted from the side-draw is 129° C., the diol content is 5.44 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 5:1. The stream entering the extractant purifier accounts for 3% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.83%, the extractant at the bottom of the separator has a purity of 99.50%, the loss rate of the extractant is 0.007%.

Example 14

According to the process flow shown in FIG. 2, the extractant is N-octane, and a ratio of the extractant and 1,2-propylene oxide is 10:1 in a feed stream containing 1,2-propylene oxide, extractant and heavy component impurities based on the percentage by weight; the number of theoretical plates of the separation column is 30, the side-draw production outlet of the separation column is located at the 2nd theoretical plate above a return port of the reboiler. The operating pressure of the separation column is 0.10 MPaA, the temperature is 68° C., the temperature of an azeotrope extracted from the side-draw is 129° C., the diol content is 5.44 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 5:1. The stream entering the extractant purifier accounts for 3% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.94%, the extractant at the bottom of the separator has a purity of 99.50%, the loss rate of the extractant is 0.008%.

Example 15

According to the process flow shown in FIG. 2, the extractant is N-octane, and a ratio of the extractant and 1,2-propylene oxide is 6:1 in a feed stream containing 1,2-propylene oxide, extractant and heavy component impurities based on the percentage by weight; the number of theoretical plates of the separation column is 30, the side-draw production outlet of the separation column is located at the $2^{nd}$ theoretical plate above a return port of the reboiler. The operating pressure of the separation column is 0.10

MPaA, the temperature is 68° C., the temperature of an azeotrope extracted from the side-draw is 129° C., the diol content is 5.44 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 5:1. The stream entering the extractant purifier accounts for 3% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.96%, the extractant at the bottom of the separator has a purity of 99.50%, the loss rate of the extractant is 0.009%.

Example 16

According to the process flow shown in FIG. 2, the extractant is N-octane, and a ratio of the extractant and 1,2-propylene oxide is 6:1 in a feed stream containing 1,2-propylene oxide, extractant and heavy component impurities based on the percentage by weight; the number of theoretical plates of the separation column is 20, the side-draw production outlet of the separation column is located at the Pt theoretical plate above a return port of the reboiler. The operating pressure of the separation column is 0.10 MPaA, the temperature is 34.1° C., the temperature of an azeotrope extracted from the side-draw is 112.8° C., the diol content is 6.86 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 5:1. The stream entering the extractant purifier accounts for 3% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.95%, the extractant at the bottom of the separator has a purity of 99.50%, the loss rate of the extractant is 0.008%.

Example 17

According to the process flow shown in FIG. 2, the extractant is N-octane, and a ratio of the extractant and 1,2-propylene oxide is 6:1 in a feed stream containing 1,2-propylene oxide, extractant and heavy component impurities based on the percentage by weight; the number of theoretical plates of the separation column is 30, the side-draw production outlet of the separation column is located at the $2^{nd}$ theoretical plate above a return port of the reboiler. The operating pressure of the separation column is 0.16 MPaA, the temperature is 47.9° C., the temperature of an azeotrope extracted from the side-draw is 134.8° C., the diol content is 8.14 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 5:1. The stream entering the extractant purifier accounts for 3% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.96%, the extractant at the bottom of the separator has a purity of 99.50%, the loss rate of the extractant is 0.007%.

Example 18

According to the process flow shown in FIG. 2, the extractant is N-octane, and a ratio of the extractant and 1,2-propylene oxide is 6:1 in a feed stream containing 1,2-propylene oxide, extractant and heavy component impurities based on the percentage by weight; the number of theoretical plates of the separation column is 40, the side-draw production outlet of the separation column is located at the 2nd theoretical plate above a return port of the reboiler. The operating pressure of the separation column is 0.32 MPaA, the temperature is 71.1° C., the temperature of an azeotrope extracted from the side-draw is 159.8° C., the diol content is 10.63 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 5:1. The stream entering the extractant purifier accounts for 3% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.97%, the extractant at the bottom of the separator has a purity of 99.50%, the loss rate of the extractant is 0.005%.

Example 19

According to the process flow shown in FIG. 2, the extractant is N-octane, and a ratio of the extractant and 1,2-propylene oxide is 6:1 in a feed stream containing 1,2-propylene oxide, extractant and heavy component impurities based on the percentage by weight; the number of theoretical plates of the separation column is 46, the side-draw production outlet of the separation column is located at the $3^{rd}$ theoretical plate above a return port of the reboiler. The operating pressure of the separation column is 0.40 MPaA, the temperature is 79.4° C., the temperature of an azeotrope extracted from the side-draw is 168.8° C., the diol content is 11.62 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 5:1. The stream entering the extractant purifier accounts for 3% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.97%, the extractant at the bottom of the separator has a purity of 99.50%, the loss rate of the extractant is 0.004%.

Example 20

According to the process flow shown in FIG. 2, the extractant is C8 saturated alkane mixture, and a ratio of the extractant and 1,2-propylene oxide is 12:1 in a feed stream containing 1,2-propylene oxide, extractant and heavy component impurities based on the percentage by weight; the number of theoretical plates of the separation column is 30, the side-draw production outlet of the separation column is located at the $2^{nd}$ theoretical plate above a return port of the reboiler. The operating pressure of the separation column is 0.28 MPaA, the temperature is 66.3° C., the temperature of an azeotrope extracted from the side-draw is 156.3° C., the diol content is 9.76 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 4:1. The stream entering the extractant purifier accounts for 8% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.95%, the extractant at the bottom of the separator has a purity of 99.50%, the loss rate of the extractant is 0.006%.

Example 21

According to the process flow shown in FIG. 2, the extractant is N-octane, and a ratio of the extractant and 1,2-propylene oxide is 6:1 in a feed stream containing 1,2-propylene oxide, extractant and heavy component impurities based on the percentage by weight; the number of theoretical plates of the separation column is 30, the side-draw production outlet of the separation column is located at the 2nd theoretical plate above a return port of the reboiler. The operating pressure of the separation column is 0.28 MPaA, the temperature is 66.3° C., the temperature of an azeotrope extracted from the side-draw is 155.6° C., the diol content is 9.88 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 4:1. The stream entering the extractant purifier accounts for 13% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.96%, the extractant at the bottom of the separator has a purity of 99.50%, the loss rate of the extractant is 0.006%.

Example 22

According to the process flow shown in FIG. 2, the extractant is N-octane, and a ratio of the extractant and 1,2-propylene oxide is 4:1 in a feed stream containing 1,2-propylene oxide, extractant and heavy component impurities based on the percentage by weight; the number of theoretical plates of the separation column is 30, the side-draw production outlet of the separation column is located at the $2^{nd}$ theoretical plate above a return port of the reboiler. The operating pressure of the separation column is 0.28 MPaA, the temperature is 66.3° C., the temperature of an azeotrope extracted from the side-draw is 154.6° C., the diol content is 9.91 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 3:1. The stream entering the extractant purifier accounts for 16% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.97%, the extractant at the bottom of the separator has a purity of 99.50%, the loss rate of the extractant is 0.006%.

Example 23

According to the process flow shown in FIG. 2, the extractant is C8 saturated alkane mixture, and a ratio of the extractant and 1,2-propylene oxide is 4:1 in a feed stream containing 1,2-propylene oxide, extractant and heavy component impurities based on the percentage by weight; the number of theoretical plates of the separation column is 30, the side-draw production outlet of the separation column is located at the $2^{nd}$ theoretical plate above a return port of the reboiler. The operating pressure of the separation column is 0.28 MPaA, the temperature is 66.3° C., the temperature of an azeotrope extracted from the side-draw is 154.6° C., the diol content is 9.91 wt %, and the diol in the side-draw is enriched and produced; the heavy component impurity stream at the bottom of the extractant purifier is enriched and extracted. The separation column reboiler A is a thermosiphon reboiler, the extractant purifier B is a kettle-type reboiler, the ratio of the heat exchange area of the reboiler A to that of the reboiler B is 2:1. The stream entering the extractant purifier accounts for 20% by weight of the total amount of the column kettle stream of the separation column.

The 1,2-propylene oxide product obtained from the top of the separation column has a purity of 99.95%, a content of water ≤10 wtppm, a content of acetaldehyde+propionaldehyde ≤10 wtppm, a content of acid ≤5 wtppm and a recovery rate of 99.97%, the extractant at the bottom of the separator has a purity of 99.50%, the loss rate of the extractant is 0.006%.

Example 24

According to the process flow chart shown in FIG. 2, the production method is performed pursuant to the process conditions described in Example 23, the differences reside in that the azeotrope produced at the side-draw is cooled and then subjected to the phases separation, the light phase is returned to the separation column, and the heavy phase is externally extracted as impurities.

The 1,2-propylene oxide product obtained from the top of the separation column has a purity of 99.99%, a content of water ≤10 wtppm, a content of acetaldehyde+propionaldehyde ≤10 wtppm, a content of acid ≤5 wtppm and a recovery rate of 99.99%, the extractant at the bottom of the separator has a purity of 99.99%, the loss rate of the extractant is 0.001%.

Comparative Example 1

According to the process flow shown in FIG. 3, the operating conditions of the separation column comprise: the temperature of vapor phase at the column top is 103° C., and the pressure is 0.22 MPaG; the extractant is N-octane, and a ratio of the extractant and 1,2-butylene oxide is 8:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 96.38%, the extractant at the bottom of the separation column has a purity of 98.0%, and the loss rate of the extractant is 2.02%.

When compared with the Example 1, the separation energy consumption for purifying 1,2-butylene oxide per ton in the Comparative Example 1 is increased by 4.5%.

Comparative Example 2

According to the process flow shown in FIG. 3, the operating conditions of the separation column comprise: the temperature of vapor phase at the column top is 103° C., and the pressure is 0.22 MPaG; the extractant is N-octane, and a ratio of the extractant and 1,2-butylene oxide is 6:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 98.50%, the extractant at the bottom of the separation column has a purity of 97.0%, and the loss rate of the extractant is 2.20%.

Comparative Example 3

According to the process flow shown in FIG. 3, the operating conditions of the separation column comprise: the temperature of vapor phase at the column top is 103° C., and the pressure is 0.22 MPaG; the extractant is N-octane, and a ratio of the extractant and 1,2-butylene oxide is 4:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 98.88%, the extractant at the bottom of the separation column has a purity of 97.5%, and the loss rate of the extractant is 2.45%.

Comparative Example 4

According to the process flow shown in FIG. 3, the operating conditions of the separation column comprise: the temperature of vapor phase at the column top is 103° C., and the pressure is 0.22 MPaG; the extractant is N-octane, and a ratio of the extractant and 1,2-butylene oxide is 3:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 97.13%, the extractant at the bottom of the separation column has a purity of 98.0%, and the loss rate of the extractant is 2.62%.

Comparative Example 5

According to the process flow shown in FIG. 3, the operating conditions of the separation column comprise: the temperature of vapor phase at the column top is 103° C., and the pressure is 0.22 MPaG; sending the heavy component impurity stream-effluent stream to be washed with water and then recycling the stream back so as to reduce the loss of the extractant; the extractant is N-octane, and a ratio of the extractant and 1,2-butylene oxide is 6:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 97.58%, the extractant at the bottom of the separation column has a purity of 97.50%, and the loss rate of the extractant is 1.72%.

When compared with the Example 1, the separation energy consumption for purifying 1,2-butylene oxide per ton in the Comparative Example 5 is increased by 6.8%.

Comparative Example 6

According to the process flow shown in FIG. 3, the operating conditions of the separation column comprise: the temperature of vapor phase at the column top is 143° C., and the pressure is 0.22 MPaG; the extractant is N-octane, and a ratio of the extractant and 1,2-butylene oxide is 8:1 in a feed stream containing 1,2-butylene oxide and extractant based on the percentage by weight; the separation column reboiler A is a forced circulation type reboiler.

The 1,2-butylene oxide stream at the top of the separation column has a purity of 99.95%, the recovery rate is 96.42%, the extractant at the bottom of the separation column has a purity of 98.5%, and the loss rate of the extractant is 1.95%.

The invention claimed is:

1. A method for producing epoxyalkane, the method comprises: separating, in a separation column, a first stream containing an epoxyalkane, an extractant, and a diol; producing an epoxyalkane product stream from the upper part of the separation column; and discharging the extractant mainly in a form of the column kettle stream from the lower part of the separation column, it is characterized in that the method further comprises producing a second stream containing an azeotrope of the extractant and the diol from the side-draw of the separation column located lower than a feed position.

2. The method according to claim 1, wherein the operating conditions of the separation column comprise: a temperature of 20-95° C.; a pressure of 0.02-0.4 MPaA; and the number of theoretical plates of the separation column is 15-80.

3. The method according to claim 1, wherein the operating conditions of the separation column comprise: a temperature of 30-85° C.; a pressure of 0.10-0.32 MPaA; and the number of theoretical plates of the separation column is 20-65.

4. The method according to claim 1, wherein the operating conditions of the separation column comprise: the number of theoretical plates of the separation column is 20-50.

5. The method according to claim 2, wherein based on the composition and distribution of the extractant in the rectification column, the position for extracting the second stream from the side-draw of the separation column is located at the $1^{st}$-$8^{th}$ plates from the bottom.

6. The method according to claim 2, wherein based on the composition and distribution of the extractant in the rectification column, the position for extracting the second stream from the side-draw of the separation column is located at the $2^{nd}$-$6^{th}$ plates from the bottom.

7. The method according to claim 2, wherein based on the composition and distribution of the extractant in the rectification column, the position for extracting the second stream from the side-draw of the separation column is located at the 2nd-4th plates from the bottom.

8. The method according to claim 2, wherein the epoxyalkane is propylene oxide, the diol is 1,2-propylene glycol, and the position where the side-draw is arranged for extracting has a temperature of 100° C. −175° C.; or
the epoxyalkane is butylene oxide, the diol is 1,2-butanediol, and the position where the side-draw is arranged for extracting has a temperature of 120° C. −150° C.

9. The method according to claim 2, wherein the epoxyalkane is propylene oxide, the diol is 1,2-propylene glycol, and the position where the side-draw is arranged for extracting has a temperature of 110° C. −170° C.; or
the epoxyalkane is butylene oxide, the diol is 1,2-butanediol, and the position where the side-draw is arranged for extracting has a temperature of 125° C. −145° C.

10. The method according to claim 1, wherein the method further comprises:
cooling the second stream extracted from the side-draw of the separation column, and performing the liquid-liquid phase separation to respectively obtain a light phase which is mainly containing the extractant and a heavy phase which is mainly containing diol; and returning the light phase to the separation column.

11. The method according to claim 1, wherein the method further comprises:
regarding a part of the column kettle stream of the separation column as a third part of the stream and introducing it into the extractant purifier for purification, respectively obtaining a vapor phase or a vapor-liquid mixture as a light component and a liquid phase as a heavy component, returning the vapor phase light component to the separation column, and introducing the liquid phase heavy component to a post-treatment.

12. The method according to claim 11, wherein the third part of the stream accounts for 2-20% by weight of the total amount of the column kettle stream of the separation column.

13. The method according to claim 11, wherein the extractant purifier is a distillation column or a reboiler.

14. The method according to claim 11, wherein the extractant purifier is a kettle-type reboiler.

15. The method according to claim 11, wherein the extractant purifier is disposed between a lower part of an inlet of the separation column for introducing a stream containing the epoxyalkane and the extractant and a column bottom of the separation column.

16. The method according to claim 13, wherein the method further comprises: sending a part of the column kettle stream to a column bottom reboiler of the separation column for heating and re-boiling, and then returning it to the separation column; the temperature difference between the stream entering the column bottom reboiler and the stream entering the extractant purifier is ≤5° C.

17. The method according to claim 13, wherein the method further comprises:
sending a part of the column kettle stream to a column bottom reboiler of the separation column for heating and re-boiling, and then returning it to the separation column; the temperature difference between the stream entering the column bottom reboiler and the stream entering the extractant purifier is ≤3° C.

18. The method according to claim 16, wherein the ratio of the heat exchange area of the column bottom reboiler to that of the reboiler as the extractant purifier is within a range of (2-5):1.

19. The method according to claim 16, wherein the bottom reboiler is any one of a thermosiphon reboiler, a kettle-type reboiler and a forced circulation type reboiler.

20. The method according to claim 1, wherein in the first stream, a ratio of the extractant to the epoxyalkane is (2-25):1.

21. The method according to claim 1, wherein in the first stream, a ratio of the extractant to the epoxyalkane is (3-20):1.

22. The method according to claim 1, wherein in the first stream, a ratio of the extractant to the epoxyalkane is (3-13):1.

23. The method according to claim 1, wherein the first stream is derived from an extraction product stream obtained by extractive distillation of an alkene epoxidation reaction product.

* * * * *